(12) United States Patent
Sharma et al.

(10) Patent No.: US 12,274,702 B2
(45) Date of Patent: Apr. 15, 2025

(54) NASAL COMPOSITIONS COMPRISING ALCAFTADINE

(71) Applicant: ALKEM LABORATORIES LIMITED, Mumbai (IN)

(72) Inventors: Akhilesh Sharma, Mumbai (IN); Babasaheb Aware, Taluka and District Beed (IN); Viraj Shah, Dist-Dhule (IN); Amol Aiwale, Pandharpur (IN)

(73) Assignee: ALKEM LABORATORIES LIMITED, Mumbai (IN)

( * ) Notice: Subject to any disclaimer, the term of this patent is extended or adjusted under 35 U.S.C. 154(b) by 0 days.

(21) Appl. No.: 18/943,210

(22) Filed: Nov. 11, 2024

(65) Prior Publication Data

US 2025/0064827 A1    Feb. 27, 2025

Related U.S. Application Data

(63) Continuation of application No. 18/549,916, filed as application No. PCT/IB2021/055221 on Jun. 14, 2021.

(30) Foreign Application Priority Data

Apr. 1, 2021  (IN) .............................. 202121015680

(51) Int. Cl.
| | | |
|---|---|---|
| *A61K 31/55* | (2006.01) | |
| *A61K 9/00* | (2006.01) | |
| *A61K 45/06* | (2006.01) | |
| *A61K 47/02* | (2006.01) | |
| *A61K 47/18* | (2017.01) | |
| *A61K 47/38* | (2006.01) | |

(52) U.S. Cl.
CPC ............ *A61K 31/55* (2013.01); *A61K 9/0043* (2013.01); *A61K 45/06* (2013.01); *A61K 47/02* (2013.01); *A61K 47/183* (2013.01); *A61K 47/186* (2013.01); *A61K 47/38* (2013.01)

(58) Field of Classification Search
CPC ........................................................ A61K 31/55
USPC ..................................................... 514/214.02
See application file for complete search history.

(56) References Cited

U.S. PATENT DOCUMENTS

| | | |
|---|---|---|
| 5,164,194 A | 11/1992 | Hettche |
| 5,468,743 A | 11/1995 | Janssens et al. |
| 8,664,215 B2 | 3/2014 | Ingerman et al. |
| 2005/0142072 A1 | 6/2005 | Birch et al. |
| 2009/0324699 A1 | 12/2009 | Preswetoff-Morath |
| 2013/0005708 A1 | 1/2013 | Lalwani |
| 2017/0065605 A1 | 3/2017 | Ingerman et al. |

FOREIGN PATENT DOCUMENTS

| | | |
|---|---|---|
| CN | 102283849 A | 12/2021 |
| WO | 2007117971 A2 | 10/2007 |
| WO | 2019022225 A1 | 1/2019 |
| WO | 2021255622 A1 | 12/2021 |

OTHER PUBLICATIONS

Bohets, et al., "Clinical Pharmacology of Alcaftadine, A Novel Antihistamine for the Prevention of Allergic Conjunctivitis", Journal of Ocular Pharmacology and Therapeutics, 2011, 27:187-195.
ISR and Written Opinion issued in PCT/IB2021/055221 on Feb. 3, 2022.
Popov et al., "Methyl-cellulose powder for prevention and management of nasal symptoms," Expert Review of Respiratory Medicine, Sep. 6, 2017, 9 pages, DOI: 10.1080/17476348.2017.1375408.
Bakhrushina, Elena, et al., "Comparative Study of the Mucoadhesive Properties of Polymers for Pharmaceutical Use", Open Access Macedonian Journal of Medical Sciences, 2020, 8(A):639-645.

*Primary Examiner* — Raymond J Henley, III
(74) *Attorney, Agent, or Firm* — Blank Rome LLP

(57) ABSTRACT

The present invention relates to a nasal pharmaceutical composition comprising alcaftadine or a pharmaceutically acceptable salt and optionally one or more pharmaceutically acceptable excipients, methods of treating allergic rhinitis, allergic rhino-conjunctivitis, or symptoms thereof (such as nasal congestion) with the nasal pharmaceutical composition, and methods of preparing it.

24 Claims, No Drawings

NASAL COMPOSITIONS COMPRISING ALCAFTADINE

The present application is a continuation of U.S. patent application Ser. No. 18/549,916, filed Sep. 10, 2023, which is the U.S. national phase of International Patent Application No. PCT/IB2021/055221, filed Jun. 14, 2021, which claims the benefit of Indian Patent Application No. 202121015680, filed Apr. 1, 2021, each of which is hereby incorporated by reference.

FIELD OF THE INVENTION

The present invention relates to a nasal pharmaceutical composition comprising alcaftadine or a pharmaceutically acceptable salt and optionally one or more pharmaceutically acceptable excipients, methods of treating allergic rhinitis, allergic rhino-conjunctivitis, or symptoms thereof (such as nasal congestion) with the nasal pharmaceutical composition, and methods of preparing it.

BACKGROUND OF THE INVENTION

Allergic rhinitis is among the most common disease affecting globally. Allergic rhinitis persists throughout the life. It has been reported that allergic rhinitis self-reported prevalence ranges from 2% to 25% in children and 1% to greater than 40% in adults. Symptoms of allergic rhinitis include sneezing, rhinorrhea, nasal itching and nasal congestion. Ocular symptoms are also common. Allergic rhino-conjunctivitis is associated with itching and redness of the eyes and tearing.

Allergic rhinitis is characterized by inflammation of the nasal mucous membranes because of a complex response to nasal allergen exposure. The levels of histamine are raised in allergic rhinitis. Allergic rhinitis is characterised by sensitization-formation and expression of antigen specific IgE, followed by inflammation in two phases viz. early and late phase. Mast cells appear to be activated during the early reaction and basophils during the late reaction. The early phase develops in 30 minutes and disappears, characterized by sneezing and rhinorrhea. The early phase response involves cross linking of IgE molecules leading to degranulation of mast cells and release of mediators such as histamine, tryptase, prostaglandins, chymase, kinins, heparins and leukotrienes. The late reaction is inflammatory in nature and shows nasal obstruction approximately six hours after exposure to allergens and subsides slowly. The late phase response is characterized by an inflammatory cellular influx of T lymphocytes, basophils and eosinophils. The late phase response involves mediators released by cells including leukotrienes, kinins, histamine, cytokines and chemokines. These mediators lead to the symptoms of rhinorhhea, nasal congestion, sneezing, itching, redness of nose, watery eyes, swelling of rhino-pharyngeal region, increase in ear pressure and postnasal drip.

Nasal congestion is one of the most common symptoms encountered in primary care and specialist clinics, and it is the symptom that is most bothersome to patients. Mucosal inflammation is responsible for many of the distinct and interrelated factors that contribute to congestion, including increased venous engorgement, elevated nasal secretions, and tissue swelling or edema.

Research shows that more than 60% of patients with allergic rhinitis are not satisfied with their current treatment, particularly due to lack of efficacy (Bousquet et al., *J Allergy Clin Immunol.*, 2009 September, 124(3):428-33).

U.S. Pat. No. 5,468,743 discloses alcaftadine and methods of treating allergic conditions.

U.S. Pat. No. 8,664,215 discloses an ophthalmic alcaftadine composition and methods of treating or preventing ocular allergy.

CN 102283849 discloses a combination of alcaftadine and pseudoephedrine as well as a combination of alcaftadine, pseudoephedrine and acetaminophen for the relief of symptoms related to allergic rhinitis and allergic conjunctivitis.

U.S. Pat. No. 5,164,194 discloses a medicament for nasal use or for use in the eye which contains as an active ingredient azelastine.

US 2009/0324699 discloses a pharmaceutical composition comprising a corticosteroid and an antihistamine, a polar lipid liposome, and a pharmaceutically acceptable aqueous carrier. However, such compositions involve use of a complex process for manufacturing such liposomes.

WO 2019/022225 describes a preservative-free aqueous pharmaceutical composition containing alcaftadine or a salt thereof at a concentration of more than 0.15% w/v.

There exists a need for intranasal compositions which provide improved relief including a faster onset of action compared to the currently available therapies.

SUMMARY OF INVENTION

The present invention relates to a nasal pharmaceutical composition, such as a nasal spray, useful for the treatment of allergic rhinitis, allergic rhino-conjunctivitis, and nasal congestion comprising alcaftadine or a pharmaceutically acceptable salt thereof and a mucoadhesive agent. The composition may be an aqueous composition and optionally includes one or more pharmaceutically acceptable excipients. The composition imparts enhanced mucoadhesion to the nasal mucosa, optimal penetration in the nasal mucosa, and minimal nasal irritation. The composition also has improved organoleptic properties that provide better patient compliance and treatment outcomes than other antihistamine products which provide an unpleasant taste, such as azelastine products. In one embodiment, the composition has a faster onset of relief compared to other nasally administered antihistamines, such as olopatadine. In one embodiment, the composition, when intranasally administered, has an onset of action in less than 15 or 10 minutes. In another embodiment, the composition is devoid of an unpleasant taste.

In one embodiment, the nasal pharmaceutical composition is an aqueous pharmaceutical composition comprising (i) about 0.1 to 1.0% w/w alcaftadine or a pharmaceutically acceptable salt thereof (such as alcaftadine) (for example, about 0.125 to 0.75% w/w alcaftadine, such as 0.125, 0.25, 0.35, 0.45, 0.5, 0.6, and 0.75% w/w), (ii) about 0.01 to 1.0% w/w hydroxypropyl methyl cellulose (HPMC) (such as an HPMC having a viscosity of 20 cPs or lower (e.g., 6 cPs)), (iii) about 0.068 to about 6.8% w/w of sodium chloride, (iv) about 0.0019 to about 0.19% w/w monobasic sodium phosphate, (v) about 0.005 to about 0.5% w/w disodium edetate (e.g., disodium edetate dihydrate), and (vi) about 0.0025 to about 0.25% w/w benzalkonium chloride. The composition may include amounts of sodium hydroxide and/or hydrochloric acid to achieve the desired pH, such as a pH of 6.5 to 7.0 or 6.3 to 7.3.

In one embodiment, the nasal pharmaceutical composition is an aqueous pharmaceutical composition comprising (1) about 0.125% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

In another embodiment, the nasal pharmaceutical composition is an aqueous pharmaceutical composition comprising (1) about 0.25% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

In yet another embodiment, the nasal pharmaceutical composition is an aqueous pharmaceutical composition comprising (1) about 0.50% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

The nasal pharmaceutical compositions described herein are stable. In one embodiment, the nasal pharmaceutical composition, after 24 hours, 3 or 6 months storage at 25° C. and 60% relative humidity or 40° C. and 75% relative humidity has at least 90, 95, or 98% of the initial amount of active ingredient (here, alcaftadine) present. In another embodiment, the amount of any single individual impurity (of the active ingredient) is no more than 0.5%, 0.2%, 0.1% or 0.05% by weight, based on the amount of active ingredient (alcaftadine) present. In yet another embodiment, the amount of total impurities (of the active ingredient) is no more than 3%, 2%, 1%, 0.5%, 0.3%, or 0.2% by weight, based on the amount of active ingredient (alcaftadine) present.

Another embodiment is a method of treating allergic rhinitis, allergic rhino-conjunctivitis, or symptoms thereof (such as nasal congestion) in a patient in need thereof by intranasally administering an effective amount of alcaftadine or a pharmaceutically acceptable salt thereof. Preferably, the nasal pharmaceutical composition of the present invention is intranasally administered. In one embodiment, the patient suffers from allergic rhinitis. In another embodiment, the patient suffers from seasonal allergic rhinitis. In yet another embodiment, the patient suffers from perennial allergic rhinitis. In yet another embodiment, the patient suffers from moderate to severe seasonal allergic rhinitis. In yet another embodiment, the patient suffers from moderate to severe perennial allergic rhinitis.

Yet another embodiment is a method of reducing the use of nasal decongestants by intranasally administering an effective amount of alcaftadine or a pharmaceutically acceptable salt thereof. Preferably, the nasal pharmaceutical composition of the present invention is intranasally administered.

Yet another embodiment is a method of inhibiting, suppressing, or preventing nasal polyps in a patient in need thereof by intranasally administering an effective amount of alcaftadine or a pharmaceutically acceptable salt thereof. Preferably, the nasal pharmaceutical composition of the present invention is intranasally administered.

The methods and nasal compositions described herein can result in better patient compliance than other treatments for allergic rhinitis as the present inventors discovered that alcaftadine, when intranasally administered does not result in an unpleasant taste as with the antihistamine azelastine.

Yet another embodiment is a method of preparing a nasal pharmaceutical composition (such as those described herein) comprising the steps of (i) dissolving a pH adjusting agent (e.g., hydrochloric acid), a tonicity adjustment agent (e.g., sodium chloride), and alcaftadine in water to form an active phase solution, (ii) mixing a mucoadhesive agent (such as HPMC) with water and then adding a chelating agent (e.g., disodium edetate such as disodium edetate dihydrate) and a buffering agent (e.g., monobasic sodium phosphate) to form a bulk solution, (iii) adding the bulk solution to the active phase solution, (iv) adding a preservative (e.g., benzalkonium chloride) to the solution prepared in step (iii), (v) optionally, adjusting the pH of the solution using sodium hydroxide (e.g., to a pH of 6.5 to 7.0 or 6.3 to 7.3), and (vi) optionally, adding water (e.g., purified water) to the solution to obtain a desired volume and/or concentration for each component.

DETAILED DESCRIPTION OF THE INVENTION

The inventors of the present invention have found that alcaftadine or a pharmaceutically acceptable salt thereof provides an advantageous composition for treatment of allergic rhinitis, allergic rhino-conjunctivitis, and symptoms thereof (such as nasal congestion). The nasal pharmaceutical composition provides a rapid onset of action, for instance within 0.15, 0.1, 0.08, or 0.05 hours. The composition provides improved relief from nasal itching and nasal decongestion. Furthermore, the composition has fewer side effects. Other antihistaminic agents have central nervous system adverse effects due to inverse agonism at $H_1$-receptors, inhibition of neurotransmission in histaminergic neurons, and impairment of alertness, cognition, learning, and memory that is not necessarily associated with sedation, drowsiness, fatigue, or somnolence. Intranasal administration of alcaftadine provides a local effect without systemic absorption and therefore without CNS side effects. For instance, an intranasal composition of alcaftadine is associated with fewer adverse reactions such as headache and epistaxis as compared to olapatadine and azelastine nasal spray.

The inventors have also found that formulating alcaftadine or a pharmaceutically acceptable salt thereof with a mucoadhesive agent improves the residence time of the composition in the nasal cavity, thereby enhancing drug absorption across nasal mucosa and relief of nasal symptoms, such as nasal congestion, compared to formulations devoid of mucoadhesive agents.

One embodiment is a nasal pharmaceutical composition of alcaftadine or a pharmaceutically acceptable salt thereof, characterized in that the composition has a faster onset of relief compared to other anti-histaminics (such as azelstine and olopatadine). In one preferred embodiment, the composition provides a rapid onset of action with a $T_{max}$ for alcaftadine of about 0.25 hours or less (such as 0.2, 0.15, 0.1, 0.08, or 0.05 hours).

In a further embodiment, the present invention provides a pharmaceutical composition of alcaftadine or a pharmaceutically acceptable salt thereof for the treatment of symptoms associated with allergic rhinitis such as sneezing, nasal itching, nasal inflammation, nasal irritation, rhinorrhea, nasal pruritus and nasal congestion. In one embodiment, the composition provides relief of more than one symptom associated with allergic rhinitis. The composition is an effective nasal decongestant. As a result, patients can reduce their concomitant use of other nasal decongestants.

The nasal pharmaceutical composition of the present invention can be administered in the nostril(s) or to the eyes once or twice a day.

Alcaftadine

Alcaftadine (6,11-dihydro-11-(1-methyl-4-piperidinylidene)-5H-imidazo[2,1-b][3]benzazepine-3-carboxaldehyde is an anti-allergic therapeutic agent that has inverse agonist effects on $H_1$, $H_2$, and $H_4$ receptors, as well as mast cell-stabilizing effects.

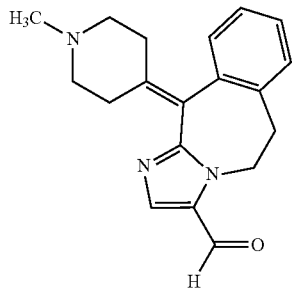 [SMILES: CN1CCC(=C2c3ccccc3CCn3c(C=O)cnc32)CC1]

$H_2$ receptors play a vital role in nasal congestion. $H_4$ receptors influence the inflammatory response (eosinophils, T cells, dendritic cells, basophils, mast cells, and sensory nerve cells). Alcaftadine has higher binding affinity to $H_1$ and $H_2$ receptors compared to other antihistamines namely azelastine and olapatadine, and demonstrates higher efficacy in controlling total nasal symptoms, including congestion. $H_1$ and $H_2$ receptor signaling contributes to pruritus, redness of nose, cytokine secretion, fibroblast proliferation, adhesion molecule expression, microvascular permeability and production of procollagens. Estelle et al., *J Allergy Clin Immunol*, 2011, 128:1139-50. $H_4$ receptor signaling has been shown to affect cytokine and chemokine release, chemotaxis, and adhesion molecule expression in allergic rhinitis in experimental allergic rhinitis model studies. Hanuskova et al., *Open Journal of Molecular and Integrative Physiology*, 2013, 3:6-14.

Dosage Form

The nasal pharmaceutical composition may be a nasal solution, nasal suspension, nasal powder, nasal spray, nasal aerosol, nasal drops, nasal ointment, nasal inhalation, or nasal gel.

In one embodiment, the nasal pharmaceutical composition comprises a therapeutically effective amount of alcaftadine (or a pharmaceutically acceptable salt thereof) in the range of 0.05% w/w to 5% w/w. For example, the topical composition may include 0.1% w/w to 4% w/w, such as 0.1% w/w to 3% w/w, 0.1% w/w to 2% w/w, or 0.1 w/w % to 1% w/w (for example, 0.125% w/w, 0.25% w/w or 0.50% w/w) of alcaftadine, based upon 100% total weight of the composition. In one embodiment, the alcaftadine is present in dissolved form in the composition.

The nasal pharmaceutical composition may include one or more pharmaceutically acceptable excipients. Suitable excipients include, but are not limited to, mucoadhesive agents, buffering agents, osmotic agents or tonicity adjustment agents, chelating agents, permeation enhancers, pH adjusting agents, suspending agents, thickening agents (or viscosity modifiers), preservatives, solubilizers, and vehicles (such as solvents).

The nasal pharmaceutical composition can include a mucoadhesive agent to provide better adherence to nasal mucosa and improve retention of alcaftadine on the nasal mucosa. Suitable mucoadhesive agents include, but are not limited to, cellulose derivatives (such as hydroxypropylmethyl cellulose (HPMC), hydroxyethylcellulose, and carboxymethylcellulose sodium), povidone, chitosan, poloxamers (Pluronic®) and natural gums (such as guar gum and xanthan gum). A preferred mucoadhesive agent is HPMC, such as HPMC having a viscosity of 20 cPs or lower (e.g., 6 cPs). In one embodiment, the mucoadhesive agent has a viscosity in the range of 1 to 20 cPs (e.g., 3 to 10 cPs) in order to irritating sensation of the nose which may occur with higher viscosity mucoadhesive agents. The mucoadhesive agents may be used in an amount from 0.01% to 10% by weight of the total composition, preferably 0.01% w/w to 1% w/w (based on the composition), such as 0.01% w/w to 0.9% w/w, 0.01% w/w to 0.7% w/w, 0.01% w/w to 0.5% w/w, 0.01% w/w to 0.3% w/w, or 0.01% w/w to 0.1% w/w. The mucoadhesive agents may be temperature dependent which upon applying or spraying in the nasal cavity form a gel on the nasal mucosa. The gel provides longer contact and retention time for the alcaftadine on the nasal mucosa thereby providing extended relief from nasal decongestion.

Suitable buffering agents include, but are not limited to, monobasic sodium phosphate, disodium hydrogen phosphate, dibasic sodium phosphate, tribasic sodium phosphate, and dibasic potassium phosphate. Buffering agents may be used in an amount from 0.009% w/w to 1.9% w/w of the composition, such as 0.0009% w/w to 0.19% w/w, 0.0009% w/w to 0.1% w/w, 0.009% w/w to 0.1% w/w, 0.007% w/w to 0.1% w/w, or 0.005% w/w to 0.1% w/w.

Osmotic agents or tonicity adjustment agents refer to agents that are specifically added to the composition to increase the solute level in the composition and contribute to achieving isotonicity of the nasal composition. Tonicity is the 'effective osmolality' and is equal to the sum of the concentrations of the solutes which have the capacity to exert an osmotic force across the membrane. Suitable tonicity adjustment agents include, but are not limited to, sodium chloride, dextrose (e.g., dextrose USP), glycerine (e.g., glycerin USP), mannitol (e.g., mannitol USP), and potassium chloride (e.g., potassium chloride USP). The tonicity adjustment agent may be used in an amount from 0.050% to 7% by weight of the total composition. In one embodiment, the nasal pharmaceutical composition contains sodium chloride in an amount sufficient to cause the composition to have a nasally acceptable osmolality, preferably 50-700 mOsmol/kg. In a preferred embodiment, the nasal pharmaceutical composition contains 0.068% w/w to 6.8% w/w of sodium chloride, based on the composition, such as 0.068% w/w to 5.8% w/w, 0.068% w/w to 4.8% w/w, 0.058% w/w to 3.8% w/w, 0.058% w/w to 2.8% w/w, or 0.058% w/w to 1.8% w/w.

Suitable chelating agents include, but are not limited to, edetate disodium, diethylene-triamine-pentaacetic acid (DTPA), iminodisuccinic acid, and ethylenediamine disuccinic acid. The chelating agent may be used in an amount from 0.005% to 0.5% by weight of the composition. In one embodiment, the composition includes edetate disodium dihydrate in the range of 0.005% w/w to 0.5% w/w, based on the composition, such as 0.005% to 0.4% w/w, 0.005% w/w to 0.3% w/w, 0.005% w/w to 0.2% w/w, or 0.005% w/w to 0.1% w/w.

The permeation enhancer can enhance the permeation of alcaftadine through the nasal mucosa. The permeation enhancer can be a hydroxyl group-containing compound. Non-limiting examples of hydroxyl group-containing compounds that may be used as permeation enhancers include alcohols (such as ethanol), diols (such as propylene glycol (also known as 1,2-propanediol), 1,3-propanediol, butylene glycol (including 1,3-butanediol, 1,2-butanediol, 2,3-butanediol, and 1,4 butanediol), hexylene glycol, dipropylene glycol, 1,5-pentanediol, 1,2-pentanediol, 1,8-octanediol, etohexadiol, p-menthane-3,8 diol, and 2-methyl-2,4-pentanediol), triols (such as glycerin), polyols (such as suitable polymers containing multiple hydroxyl groups) (including polyethylene glycols (PEGs), polypropylene glycols, polysorbates, and sorbitan esters, and suitable sugar alcohols), cyclitols (such as pinitol, insoitol), cyclic diols (such as cyclohexane diol), aromatic diols (such as hydroquinone, bisphenol A, resorcinol and catechol) or any combination thereof. Other permeation enhancer include, but are not limited to, bile salts, Vitamin E TPGS, Alkyl Maltosides, non-ionic, anionic or amphoteric surfactants having HLB value 8-14 or combination thereof. The non-limiting examples of such permeation enhancers are sodium glycocholate, sodium taurocholate, dodecyl maltosides, tridecyl maltoside or tetradecyl maltosides, or any combination thereof. In one embodiment, the permeation enhancer may be present in the nasal pharmaceutical composition in an amount from 0.5% to 50% by weight of the total composition, such as 2% w/w, 5% w/w, 7.5% w/w, 10% w/w, 20% w/w, and 40% w/w.

Suitable pH adjusting agents include, but are not limited to hydrochloric acid, sodium hydroxide, ammonium hydroxide, magnesium hydroxide, sulphuric acid, phosphoric acid, citric acid, malic acid, and tartaric acid. Preferred pH adjusting agents include hydrochloric acid and sodium hydroxide. The pH adjusting agent may be used in an amount sufficient to obtain a pH of about 3 to about 11, such as about 5 to about 9, about 6 to about 8, about 6.3 to about 7.3, or about 6.7 to about 7.3.

Suitable preservatives include, but are not limited to, benzalkonium chloride, potassium sorbate, methyl paraben, propyl paraben, chlorbutol, chlorocresol, chlorhexidine, sodium benzoate, benzyl alcohol, and propylene glycol. In one embodiment, preservatives may be used in an amount from 0.0025% to 2.5% by weight of the total composition. In another embodiment, the composition contains 0.0025% w/w to 0.25% w/w of a preservative, based on the weight of the composition, such as 0.0025% w/w to 0.15% w/w, 0.0025% w/w to 0.1% w/w, or 0.0025% w/w to 0.05% w/w. In one preferred embodiment, the composition includes benzalkonium chloride. In one embodiment, the composition includes from 0.0025% w/w to 2.5% w/w benzalkonium chloride, based on the weight of the composition.

In another embodiment, the nasal pharmaceutical composition is preservative-free.

Suitable vehicles and solubilizers include, but are not limited to, purified water, glycols such as propylene glycol, polyethylene glycol, polypropylene glycol, glycol ether, glycerol, polyoxyethylene alcohols and polyoxyethylene fatty acid esters. The vehicle or solubilizer may be present in the composition in an amount from 5% w/w to 20% w/w, based on the weight of the composition, such as 5% w/w to 15% w/w, 5% w/w to 10% w/w, or 5% w/w to 7% w/w. Propylene glycol and polyethylene glycol may be used in an amount from 5% w/w to 20% w/w of the total composition. Purified water may be used in an amount to make the formulation 100% by weight of the total composition.

In one embodiment, the nasal pharmaceutical composition has an osmolality of 50 to 700 mOsmol/kg, such as 100 to 600 mOsmol/kg or 100 to 500 mOsmol/kg.

In one embodiment, the nasal pharmaceutical composition (e.g., a nasal solution) has a viscosity of about 1.5 to about 4 cPs, preferably about 2 cPs. The viscosity can be measured with a Brookfiled (DV II+ Pro) AD-VS-02, with a ULA spindle and a 10 mL sample at a 100 rpm, ambient temperature, and a 60 second measurement time. The viscosity measurement can be the average of three measurements.

In one embodiment, the pH of the nasal pharmaceutical composition ranges from about 3.5 to about 11. In a preferred embodiment, the pH is in the range of about 3 to about 11, preferably in the range of about 5 to about 9, more preferably in the range of about 6 to about 8, more preferably in the range of about 6.3 to about 7.3. In another embodiment, the pH of the nasal pharmaceutical composition ranges from about 6 to about 8, such as at about 6.7 to 7.3 (such as 6.8, 6.9, 7.0, 7.1, or 7.2). The nasal pharmaceutical composition may include a buffering agent in an effective amount to maintain the pH at about 3 to about 11, about 6 to about 8, or about 6.7 to 7.3 (such as 6.8, 6.9, 7.0, 7.1, or 7.2).

Yet another embodiment is an aqueous pharmaceutical composition for nasal administration to a patient comprising (1) about 0.125% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

Yet another embodiment is an aqeuous pharmaceutical composition for nasal administration to a patient comprising (1) about 0.25% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

Yet another embodiment is an aqeuous pharmaceutical composition for nasal administration to a patient comprising (1) about 0.50% w/w alcaftadine, (2) about 0.0125% w/w benzalkonium chloride, (3) about 0.050% w/w disodium edetate, (4) about 0.019% w/w monobasic sodium phosphate, (5) about 0.68% w/w sodium chloride, (6) about 0.1% w/w hydroxypropyl methyl cellulose, and (7) about 0.25% w/w hydrochloric acid.

In one embodiment, the nasal pharmaceutical compositions described herein has a droplet size distribution at 3 cm with a D10 of no more than 40 μm (e.g., from about 5 to about 30 μm), D50 of no more than 80 μm (e.g., from about 10 to about 50 μm), a D90 of no more than 180 μm (e.g., from about 40 to about 100 μm), and/or a SPAN of no more than 3 (e.g., from about 1.0 to about 3.0). In one embodiment, the spray content uniformity is from about 85 to about 115%.

In another embodiment, the nasal pharmaceutical composition of the present invention has a spray pattern at 3 cm with a $D_{max}$ of no more than 75 mm (e.g., about 20 to about 75 mm), a $D_{min}$ of no more than 50 mm (e.g., about 15 to about 50 mm), an ovality of no more than 2.0 (e.g., about 0.5 to about 2.0), and an area of no more than 2000 mm². In yet another embodiment, the nasal pharmaceutical composition of the present invention has a spray pattern at 6 cm with a $D_{max}$ of no more than 100 mm (e.g., about 50 to about 100 mm), a $D_{min}$ of no more than 75 mm (e.g., about 40 to about 75 mm), an ovality of no more than 2.0 (e.g., about 0.5 to about 2.0), and an area of no more than 5000 mm².

Preparation Method

One embodiment is a method of preparing a nasal pharmaceutical composition (such as those described herein) comprising the steps of (i) dissolving a pH adjusting agent (e.g., hydrochloric acid), a tonicity adjustment agent (e.g., sodium chloride), and alcaftadine in water to form an active phase solution, (ii) mixing a mucoadhesive agent (such as HPMC) with water and then adding a chelating agent (e.g., disodium edetate such as disodium edetate dihydrate) and a buffering agent (e.g., monobasic sodium phosphate) to form a bulk solution, (iii) adding the bulk solution to the active phase solution, (iv) adding a preservative (e.g., benzalkonium chloride) to the solution prepared in step (iii), (v) optionally, adjusting the pH of the solution using sodium hydroxide (e.g., to a pH of 6.5 to 7.0 or 6.3 to 7.3), and (vi) optionally, adding water (e.g., purified water) to the solution to obtain a desired volume and/or concentration for each component.

In a further embodiment of the present invention, the nasal pharmaceutical composition is in the form of an aerosol or a solution which includes a delivery system, such as a bottle or a pump delivery or a high-density polyethylene container equipped with a nasal spray pump, metered-dose spray pump, inhaler, with dropper and other forms for intra-nasal usage. The composition can be delivered in a mist of spray droplets or minor droplets to coat the nasal mucosa upon administration. Preferred pumps for use in such products of the invention are metered multi-dose pumps. The selection of the pump is based on the desired dose per spray volume and spray pattern appropriate for topical delivery to the nasal mucosa. The dosage per spray may range from 1 ml to 100 ml, where each spray may deliver 100 µl to 400 µl per spray.

Compositions prepared by the process as described herein can withstand the accelerated stability conditions of temperature and relative humidity and maintain their physical and chemical integrity at accelerated conditions of stability.

Methods of Treatment

Another embodiment is a method of treating allergic rhinitis, allergic rhino-conjunctivitis, or symptoms thereof (such as nasal congestion) in a patient in need thereof by intranasally administering an effective amount of alcaftadine or a pharmaceutically acceptable salt thereof (such as a nasal pharmaceutical composition comprising alcaftadine or a pharmaceutically acceptable salt thereof). Preferably, the nasal pharmaceutical composition of the present invention is intranasally administered. In one embodiment, the patient suffers from allergic rhinitis. In another embodiment, the patient suffers from seasonal allergic rhinitis. In yet another embodiment, the patient suffers from perennial allergic rhinitis. In yet another embodiment, the patient suffers from moderate to severe seasonal allergic rhinitis. In yet another embodiment, the patient suffers from moderate to severe perennial allergic rhinitis. In one embodiment, the nasal pharmaceutical composition is intranasally administered as 1 or 2 sprays per nostril of the patient once daily. In another embodiment, the nasal pharmaceutical composition is intranasally administered as 1 or 2 sprays per nostril of the patient twice daily. Each spray of the nasal pharmaceutical composition may comprise about 171.25 mcg, about 342.5 mcg, about 685 mcg of alcaftadine.

The nasal pharmaceutical composition of the present invention can be administered in the nostril(s) or to the eyes once or twice a day. In one embodiment, from about 340 to about 5500 mcg of alcaftadine is administered daily (such as in one dose once daily, or in two equally divided doses twice daily). For instance, from about 170 to about 2740 mcg of alcaftadine can be administered to each nostril daily.

In one embodiment, one spray of a nasal pharmaceutical composition containing alcaftadine (such as described herein) is administered per nostril once per day.

In another embodiment, two sprays of a nasal pharmaceutical composition containing alcaftadine (such as described herein) are administered per nostril once per day.

In yet another embodiment, one spray of a nasal pharmaceutical composition containing alcaftadine (such as described herein) is administered per nostril twice per day.

In yet another embodiment, two sprays of the nasal pharmaceutical composition described herein are administered per nostril twice per day.

Each spray of the nasal pharmaceutical composition may provide from about 170 to about 685 mcg of alcaftadine (on a free base basis), such as about 171.25, 342.5, or 685 mcg of alcaftadine.

In one embodiment, from about 170 to about 1370 mcg alcaftadine are administered once or twice daily to each nostril. In another embodiment, about 171.25, 342.5, 685, or 1370 mcg of alcaftadine is administered to each nostril once daily. In yet another embodiment, about 171.25, 342.5, 685, or 1370 mcg of alcaftadine is administered to each nostril twice daily.

In one embodiment of the methods described herein, from about 340 to about 5480 mcg of alcaftadine are administered daily to a patient in need thereof. In another embodiment, from about 340 to about 1370 mcg of alcaftadine are administered daily to a patient in need thereof. In yet another embodiment, from about 340 to about 690 mcg of alcaftadine are administered daily to a patient in need thereof.

In one embodiment, the patient is 6 to 17 years of age. In another embodiment, the patient is 17 or 18 years of age or older.

Definitions

By "pharmaceutically acceptable excipients", it is meant any of the components of a pharmaceutical composition other than the active ingredients and which are approved by regulatory authorities or are generally regarded as safe for human or animal use.

As used herein, the term "mucoadhesion" refers to adhesion or adherence of a substance to a mucous membrane within the nasal mucosa. In the context of the present invention, the mucoadhesion is intended to convey a material that is capable of adhering to the nasal mucosa when placed in contact with that surface in order to enable compositions of the invention to adhere to that surface. Such materials are hereinafter referred to together as "mucoadhesives" or "mucoadhesive agents."

The term "allergic rhinitis" includes allergic reactions of the nasal mucosa and includes hay fever, seasonal allergic rhinitis, and perennial rhinitis (non-seasonal allergic rhinitis) which are characterized by seasonal or perennial sneezing, rhinorrhea, nasal congestion, pruritus and eye itching, redness and tearing.

The term "patient" or "subject" refers to a human patient unless indicated otherwise. The patient can be 12 years of age or older or 18 years of age or older. The patient can also be 6 to 17 years of age.

The terms "treat," "treatment," and "treating" in the context of the administration of a therapy to a patient refers to the reduction or inhibition of the progression and/or duration of a disease or condition, the reduction or amelioration of the severity of a disease or condition, and/or the amelioration of one or more symptoms thereof resulting from the administration of one or more therapies.

An "effective amount" is an amount sufficient for a compound to accomplish a stated purpose relative to the absence of the compound (e.g. reduce one or more symptoms of a disease or condition). An example of an "effective amount" is an amount sufficient to contribute to the treatment, prevention, delay, inhibition, suppression, or reduction of a symptom or symptoms of a disease or disorder, which could also be referred to as a "therapeutically effective amount." A "reduction" of a symptom or symptoms (and grammatical equivalents of this phrase) means decreasing of the severity or frequency of the symptom(s), or elimination of the symptom(s). An "effective amount" of a drug can be an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). Dosages may be varied depending upon the requirements of the patient and the compound being employed. The dose administered to a patient, in the context of the present disclosure, should be sufficient to effect a beneficial therapeutic response in the patient over time. The size of the dose may also be determined by the existence, nature, and extent of any adverse side-effects. Determination of the proper dosage for a particular situation is within the skill of the practitioner.

As used herein, unless indicated otherwise, the term "stable" refers to a pharmaceutical composition of the present invention, which after 3 or 6 months storage at 25° C. and 60% relative humidity or 40° C. and 75% relative humidity has at least 90, 95, or 98% of the initial amount of active ingredient (here, alcaftadine) present.

As used herein, the term "salts" or "pharmaceutically acceptable salt", it is meant those salts, solvate and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include hydrochloride, furoate, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include sodium, calcium, potassium and magnesium salts.

The transitional term "comprising," which is synonymous with "including," "containing," or "characterized by," is inclusive or open-ended and does not exclude additional, unrecited elements or method steps. The specification will be understood to also include embodiments which have the transitional phrase "consisting of" or "consisting essentially of" in place of the transitional phrase "comprising." The transitional phrase "consisting of" excludes any element, step, or ingredient not specified in the claim, except for impurities associated therewith. The transitional phrase "consisting essentially of" limits the scope of a claim to the specified materials or steps "and those that do not materially affect the basic and novel characteristic(s)" of the claimed invention.

The present invention is further illustrated by reference to the following examples which is for illustrative purpose only and does not limit the scope of the invention in any way.

Examples 1A-1I

The aqueous compositions shown in Tables 1A and 1B below were prepared.

TABLE 1A

| Ingredient | 1A (% w/w) | 1B (% w/w) | 1C (% w/w) | 1D (% w/w) | 1E (% w/w) |
| --- | --- | --- | --- | --- | --- |
| Alcaftadine | 0.125 | 0.25 | 0.50 | 0.5 | 0.5 |
| Benzalkonium chloride (50%)* | 0.025 | 0.025 | 0.025 | 0.025 | 0.025 |
| Disodium Edetate | 0.050 | 0.050 | 0.050 | 0.050 | 0.050 |
| Monobasic sodium Phosphate | 0.019 | 0.019 | 0.019 | 0.019 | 0.019 |
| Sodium Chloride | 0.68 | 0.68 | 0.68 | 0.68 | 0.68 |
| Hydroxypropyl methylcellulose 2910 | 0.1 | 0.1 | 0.1 | — | — |
| Sodium Carboxymethylcellulose | — | — | — | 0.1 | — |
| Povidone | — | — | — | — | 0.1 |
| Hydroxypropylcellulose-L | — | — | — | — | — |
| Hydrochloric acid | 0.25 | 0.25 | 0.25 | 0.25 | 0.25 |
| Sodium Hydroxide | q.s. | q.s. | q.s. | q.s. | q.s. |
| Purified water | q.s. | q.s. | q.s. | q.s. | q.s. |

TABLE 1B

| Ingredient | 1F (% w/w) | 1G (% w/w) | 1H (% w/w) | 1I (% w/w) |
| --- | --- | --- | --- | --- |
| Alcaftadine | 0.25 | 0.25 | 0.25 | 0.5 |
| Benzalkonium chloride (50%) | 0.025 | 0.025 | 0.025 | 0.025 |
| Disodium Edetate | 0.050 | 0.050 | 0.050 | 0.050 |
| Monobasic sodium Phosphate | 0.019 | 0.019 | 0.019 | 0.019 |
| Sodium Chloride | 0.68 | 0.68 | 0.68 | 0.68 |
| Hydroxypropyl methylcellulose 2910 | — | — | — | — |
| Sodium Carboxymethylcellulose | 0.1 | — | — | — |
| Povidone | — | 0.1 | — | — |
| Hydroxypropylcellulose-L | — | — | 0.1 | 0.1 |
| Hydrochloric acid | 0.25 | 0.25 | 0.25 | 0.25 |
| Sodium Hydroxide | q.s. | q.s. | q.s. | q.s. |
| Purified water | q.s. | q.s. | q.s. | q.s. |

Examples 1A through 1I include 0.0125% w/w of benzalkonium chloride since it is incorporated into the composition in the form of a 50% benzalkonium chloride solution.

Examples 1A-1I were prepared as follows:
a) Preparation of Active Phase Solution: Hydrochloric acid, sodium chloride, and alcaftadine were added to a suitable quantity of purified water and stirred to obtain a clear Active Phase Solution.
b) For aqueous compositions containing them, hypromellose 2910, sodium carboxymethylcellulose, povidone, or hydroxypropylcellulose-L (low-substituted hydroxypropyl cellulose) was added to a suitable quantity of purified water and stirred to obtain a clear solution.
c) Disodium edetate and monobasic sodium phosphate were added to the solution prepared in step (b), and stirred to obtain a clear Second Solution.
d) The Second Solution from step (c) was added to the Active Phase Solution of step (a) under stirring to obtain a clear solution. The container of the Second Solution was rinsed with purified water and stirred to obtain a clear solution, and then also added to the Active Phase Solution.
e) Benzalkonium chloride was added to the solution prepared in step (d) and stirred to obtain a uniform solution.
f) The pH of the solution prepared in step (e) was adjusted to 6.3 to 7.3 using sodium hydroxide (1M).
g) Purified water was added to the solution of step (f) to obtain the desired concentrations and volume.

Each spray of Examples 1A-1I can provide 137 µL of the composition, which would provide 171.25, 342.5, or 685 mcg of alcaftadine for the compositions containing 0.125, 0.25, and 0.5% w/w alcaftadine, respectively.

The stability of Examples 1A-1I was assessed by measuring the amount of impurities, pH, viscosity, and osmolality initially and after 3 and 6 months (3M and 6M) storage at 25° C. and 60% relative humidity (RH) or 40° C. and 75% RH. The results are shown in Table 1C below.

TABLE 1C

| Examples | Condition | Related Substances (% w/w) | | pH | Viscosity (cP) | Osmolality (Osmol/Kg) |
|---|---|---|---|---|---|---|
| | | Any Individual Impurity | Total Impurities | | | |
| 1A | Initial | 0.042 | 0.171 | 7.17 | 1.83 | 0.275 |
| | 25° C./60% RH (3 M) | 0.043 | 0.105 | 7.14 | 1.98 | 0.303 |
| | 25° C./60% RH (6 M) | 0.029 | 0.086 | 7.15 | 1.95 | ND |
| | 40° C./75% RH (3 M) | 0.042 | 0.112 | 7.15 | 1.94 | 0.289 |
| | 40° C./75% RH (6 M) | 0.029 | 0.125 | 7.16 | 1.93 | ND |
| 1B | Initial | 0.033 | 0.085 | 7.24 | 1.88 | 0.276 |
| | 25° C./60% RH (3 M) | 0.041 | 0.138 | 6.96 | 1.95 | 0.266 |
| | 25° C./60% RH (6 M) | 0.030 | 0.046 | 7.02 | 1.996 | 0.287 |
| | 40° C./75% RH (3 M) | 0.040 | 0.161 | 6.99 | 1.97 | 0.260 |
| | 40° C./75% RH (6 M) | 0.044 | 0.089 | 7.02 | 1.94 | 0.305 |
| 1C | Initial | 0.050 | 0.091 | 7.17 | 1.84 | 0.271 |
| | 25° C./60% RH (3 M) | 0.042 | 0.123 | 7.06 | 1.95 | 0.272 |
| | 25° C./60% RH (6 M) | 0.042 | 0.058 | 7.10 | 1.81 | 0.283 |
| | 40° C./75% RH (3 M) | 0.044 | 0.134 | 7.05 | 1.95 | 0.276 |
| | 40° C./75% RH (6 M) | 0.037 | 0.079 | 7.15 | 1.83 | 0.310 |
| 1D | Initial | 0.053 | 0.082 | 6.96 | 3.34 | 0.268 |
| | 25° C./60% RH (3 M) | 0.042 | 0.085 | 6.93 | 3.07 | 0.318 |
| | 25° C./60% RH (6 M) | 0.042 | 0.181 | 6.97 | 3.16 | 0.3 |
| | 40° C./75% RH (3 M) | 0.039 | 0.073 | 6.93 | 3.08 | 0.306 |
| | 40° C./75% RH (6 M) | 0.070 | 0.232 | 6.95 | 3.07 | 0.299 |
| 1E | Initial | 0.056 | 0.069 | 7 | 1.76 | 0.266 |
| | 25° C./60% RH (3 M) | 0.043 | 0.086 | 6.95 | 1.82 | 0.302 |
| | 25° C./60% RH (6 M) | 0.043 | 0.185 | 6.96 | 1.82 | 0.301 |
| | 40° C./75% RH (3 M) | 0.044 | 0.092 | 7.00 | 1.83 | 0.307 |
| | 40° C./75% RH (6 M) | 0.042 | 0.242 | 6.96 | 1.79 | 0.292 |
| 1F | Initial | 0.056 | 0.083 | 7.11 | 3.54 | 0.273 |
| | 25° C./60% RH (3 M) | 0.041 | 0.073 | 7.16 | 3.52 | 0.305 |
| | 25° C./60% RH (6 M) | 0.043 | 0.175 | 7.12 | 3.46 | 0.292 |
| | 40° C./75% RH (3 M) | 0.041 | 0.072 | 7.18 | 3.43 | 0.307 |
| | 40° C./75% RH (6 M) | 0.040 | 0.224 | 7.16 | 3.15 | 0.332 |
| 1G | Initial | 0.051 | 0.084 | 7.27 | 1.70 | 0.272 |
| | 25° C./60% RH (3 M) | 0.036 | 0.098 | 7.15 | 1.79 | 0.309 |
| | 25° C./60% RH (6 M) | 0.043 | 0.183 | 7.12 | 1.80 | 0.295 |
| | 40° C./75% RH (3 M) | 0.041 | 0.134 | 7.19 | 1.78 | 0.309 |
| | 40° C./75% RH (6 M) | 0.042 | 0.204 | 7.14 | 1.83 | 0.304 |
| 1H | Initial | 0.040 | 0.040 | 7.09 | 1.8 | 0.261 |
| | 25° C./60% RH (3 M) | 0.034 | 0.099 | 7.14 | 1.86 | 0.272 |
| | 25° C./60% RH (6 M) | 0.041 | 0.136 | 7.04 | 1.92 | 0.273 |
| | 40° C./75% RH (3 M) | 0.043 | 0.163 | 7.15 | 1.87 | 0.272 |
| | 40° C./75% RH (6 M) | 0.042 | 0.162 | 7.01 | 1.93 | 0.249 |
| 1I | Initial | 0.044 | 0.085 | 7.00 | 1.79 | 0.268 |
| | 25° C./60% RH (3 M) | 0.043 | 0.135 | 7.18 | 1.84 | 0.267 |
| | 25° C./60% RH (6 M) | 0.042 | 0.145 | 7 | 1.94 | 0.263 |
| | 40° C./75% RH (3 M) | 0.042 | 0.158 | 7.15 | 1.87 | 0.267 |
| | 40° C./75% RH (6 M) | 0.042 | 0.193 | 6.99 | 1.95 | 0.254 |

ND = Not determined

The spray patterns for the aqueous compositions in Examples 1A-1C were tested and the results are report in Table 1D below. In particular, the spray content uniformity (SCU), pump delivery, and droplet size distribution (DSD) were measured.

TABLE 1D

| Examples | Condition | SCU Beginning Life % | Pump delivery Shot weight Avg. (mg) | DSD (3 cm) D10 (μm) | D50 (μm) | D90 (μm) | SPAN |
|---|---|---|---|---|---|---|---|
| 1A | Initial | 99.12 | 137.78 | 15.7 | 34.3 | 73.9 | 1.7 |
|  | 25° C./60% RH (3 M) | 96.78 | 138.56 | 12.21 | 29.71 | 70.36 | 1.950 |
|  | 25° C./60% RH (6 M) | 101.6 | 139.2 | 13.41 | 32.13 | 75.85 | 1.940 |
|  | 40° C./75% RH (3 M) | 98.20 | 139.12 | 12.73 | 30.94 | 75.21 | 2.000 |
|  | 40° C./75% RH (6 M) | 94.50 | 137.13 | 15.8 | 35.2 | 75.7 | 1.7 |
| 1B | Initial | 96.97 | 137.81 | 15.5 | 33.08 | 70.75 | 1.67 |
|  | 25° C./60% RH (3 M) | ND | 137.36 | 12.64 | 30.67 | 72.03 | 1.930 |
|  | 25° C./60% RH (6 M) | 97.44 | 137.42 | 12.63 | 31.04 | 73.69 | 1.960 |
|  | 40° C./75% RH (3 M) | ND | 138.32 | 12.38 | 30.16 | 71.88 | 1.970 |
|  | 40° C./75% RH (6 M) | 97.71 | 138.19 | 12.26 | 30.93 | 75.37 | 2.04 |
| 1C | Initial | 95.33 | 137.23 | 15.7 | 34.3 | 73.95 | 1.7 |
|  | 25° C./60% RH (3 M) | ND | 137.32 | 12.63 | 30.46 | 72.47 | 1.960 |
|  | 25° C./60% RH (6 M) | 96.50 | 137.07 | 12.04 | 29.64 | 72.00 | 2.020 |
|  | 40° C./75% RH (3 M) | ND | 139.64 | 12.53 | 30.64 | 73.80 | 2.000 |
|  | 40° C./75% RH (6 M) | 96.20 | 138.44 | 11.75 | 28.85 | 68.09 | 1.95 |

Example 2: Mucoadhesive Property Measurement

The possible role of surface energy thermodynamics in mucoadhesion was investigated by measuring the contact angle of Examples 1C, 1D, 1E, and 1I, each of which contained one of hydroxypropylmethylcellulose (HPMC), sodium carboxymethyl cellulose, polyvinyl pyrrolidone, and hydroxypropylcellulose. The contact angle of each composition was measured with an instrument Kruss Model-DSA100, CN membrane (0.45 micron 47 mm; Make: MDI). For the analysis, 17 microlitres of each sample was passed through the instrument syringe to form a liquid drop on the CN membrane to measure the contact angle. The results are provided in Table 2 below.

TABLE 2

| Sample | Contact Angle (in degrees) |
|---|---|
| Example 1C | 102.88 |
| Example 1D | 104.62 |
| Example 1E | 108.41 |
| Example 1I | 109.92 |

A lower contact indicates better adherence to the membrane and therefore better mucoadhesion. HPMC resulted in superior mucoadhesion compared to the other polymers.

Example 3: Bitterness Evaluation

The aqueous composition of Example 1A was evaluated for bitterness and compared to a similar formulation without alcaftadine (placebo formulation) and three commercial intransal products (Astelin®, Patanase®, and Azep®). The compositions were evaluated in 20 volunteers according to the evaluation criteria shown in Table 3 below.

TABLE 3

| Evaluation Criteria | Score |
|---|---|
| Very much bitter | 4 |
| Bitter | 3 |
| Moderate bitter | 2 |
| No bitterness | 1 |

The results are shown in Table 4 below.

TABLE 4

| Test No. | Product name | Active | Taste score | Evaluation |
|---|---|---|---|---|
| 1 | Alcaftadine | Alcaftadine | 1 | No bitterness |
| 2 | Placebo composition of the Alcaftadine formulation | None | 1 | No bitterness |
| 3 | Astelin ® | Azelastine hydrochloride | 4 | Very much bitter |
| 4 | Patanase ® | Olopatadine hydrochloride | 2 | Moderately bitter |
| 5 | Azep ® | Azelastine hydrochloride | 4 | Very much bitter |

Alcaftadine was found to have a more acceptable taste compared to azelastine hydrochloride and olopatadine hydrochloride.

Example 4: Pharmacokinetics of Intranasal Alcaftadine

The nasal formulations of Example 1A, 1B and 1C

The pharmacokinetic profiles for Example 1A, 1B and 1C as well as an olapatdine nasal formulation were each determined on 6 male New Zealand white rabbits. The olopatadine nasal formulation (0.6% w/v) was prepared from Olopat Max® 0.7% w/v, where Olopat Max® was diluted to 0.6% w/v by using purified water.

The study was carried out on total 24 male New Zealand white rabbits, which were segregated into four groups (G1 to G4, 6 rabbits/group). Mild anaesthesia was induced in all rabbits by inhalation of 2% isoflurane. Three groups (G1-G3) of anaesthetized rabbits were intranasally administered 250 μL of alcaftadine once daily using the formulations of Examples 1A, 1B, and 1C. A comparator, 250 μL of olopatadine at a concentration of 0.6% w/v, was intranasally administered once-daily to a fourth group G4 of anaesthetized rabbits.

Sampling details for the test and reference formulations: Approximately 0.5 mL of blood sample from each rabbit was withdrawn via marginal car vein into pre-labelled Eppendorf tubes containing 10% EDTA as an anticoagulant. Blood samples were withdrawn at 0 min, 5 min, 10 min, 15 min, 30 min, 60 min, 120 min, 240 min, 480 min and 1440 min after administration of test and reference formulations.

Procedure for sample preparation: Collected blood samples were mixed gently and kept on crushed ice. Plasma samples were separated after centrifugation at 3500 rpm for 10 min at 4° C. Plasma separation was carried out within 30 min of sample collection and stored at −70±10° C. The animals were euthanized by intravenous administration of sodium thiopental injection overdose and nasal epithelium was collected. Half of the tissues of nasal epithelium were homogenized using phosphate buffered solution (20% homogenation) for quantification of alcaftadine and olopatidine. The remaining half of the tissues were stored in 10% neutral buffered formalin for detailed gross histopathological examination such as necrosis, inflammation or any changes during necropsy.

Rabbit plasma and nasal epithelial tissue concentrations of alcaftadine or olopatidine were determined using a fit-for-purpose LC-MS/MS method with LLOQ of 0.500 ng/ml or 0.250 ng/mL, respectively. The pharmacokinetic parameters were evaluated using Phoenix WinNonlin® Ent-Version 8.0 by non-compartmental analysis.

Results: The time to reach peak concentration following administration of 1.5 mg of olopatadine to New Zealand rabbits was 0.38 hours after a single administration. After a single intranasal instillation of alcaftadine at a doses of 0.312 mg, 0.625 mg and 1.25 mg, the time to achieve maximum concentration ($T_{max}$) was found to be 0.08 hours in all three groups. $T_{max}$ was achieved much earlier than olopatdine at a dose of 1.5 mg. Thus, intranasal alcaftadine exhibited a faster onset of action than intranasal olopatadine.

After a single administration of alcaftadine at a doses of 0.625 to 1.25 mg, the area under the curve ($AUC_{0-24h}$) and peak plasma concentrations ($C_{max}$) were dose proportional.

Following intranasal administration of alcaftadine at doses of 0.312 mg, 0.625 mg and 1.25 mg to rabbits, no signs or symptoms of inflammation or irritation were observed in any of the three groups. On histopathological examination, minimum to mild inflammatory cell (lymphocytes/heterophils) infiltration and increased mucous secretion in nasal epithelium was observed in a few animals across the groups administered the test and reference formulations.

The plasma concentration of alcaftadine was found to be dose proportional with overall low systemic exposure.

Example 5

The aqueous alcaftadine composition shown in Table 5 below can be prepared as described for Examples 1A-1I. The pH of the composition can be 6.3-7.3.

TABLE 5

| Ingredient | % w/w |
| --- | --- |
| Alcaftadine | 0.1 to 1.0 (such as 0.125 to 0.75, for example, 0.125, 0.25, 0.35, 0.45, 0.5, 0.6, and 0.75) |
| Hydroxypropylmethyl cellulose | 0.01 to 1 |
| Sodium chloride | 0.068 to 6.8 |
| Monobasic sodium phosphate | 0.0019 to 0.19 |
| Edetate Disodium, Dihydrate | 0.005 to 0.5 |
| Sodium hydroxide | q.s. to pH |
| Hydrochloric acid | 0.025 to 2.5 |
| Benzalkonium chloride | 0.0025 to 0.25 |
| Purified water | q.s. |

Although the inventions herein have been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described.

All publications, patents, and patent applications cited in this application are herein incorporated by reference to the same extent as if each individual publication, patent, or patent application was specifically and individually indicated to be incorporated herein by reference.

The invention claimed is:

1. A method of treating seasonal allergic rhinitis in a human patient in need thereof comprising nasally administering once daily to the patient an effective amount of an aqueous pharmaceutical composition comprising 0.125% to 0.75% w/w alcaftadine or a pharmaceutically acceptable salt thereof and a mucoadhesive agent.

2. The method of claim 1, wherein the alcaftadine is in free form.

3. The method of claim 1, wherein the mucoadhesive agent is selected from hydroxypropylmethyl cellulose, hydroxyethylcellulose, carboxymethylcellulose sodium, povidone, chitosan, guar gum, xanthan gum, and any combination of any of the foregoing.

4. The method of claim 1, wherein the mucoadhesive agent is hydroxypropylmethyl cellulose.

5. The method of claim 1, wherein the mucoadhesive agent has a viscosity of 1 to 20 cPs.

6. The method of claim 1, wherein the composition further comprises a preservative.

7. The method of claim 1, wherein the composition further comprises at least 0.0125% w/w benzalkonium chloride, based upon the total weight of the composition.

8. The method of any claim 1, wherein the composition further comprises a buffering agent, a tonicity adjustment agent, a chelating agent, or any combination of any of the foregoing.

9. The method of claim 8, wherein the buffering agent is monobasic sodium phosphate.

10. The method of claim 8, wherein the tonicity adjustment agent is sodium chloride.

11. The method of claim 8, wherein the chelating agent is disodium edetate.

12. The method of claim 1, wherein the viscosity of the composition is from about 1.5 to about 4.0 cPs.

13. The method of claim 1, wherein the pH of the composition is from about 6.3 to about 7.3.

14. The method of claim 1, wherein the composition, when intranasally administered, has an onset of action in less than 15 minutes.

15. The method of claim 1, wherein the composition comprises (i) 0.125% to 0.75% w/w alcaftadine or a pharmaceutically acceptable salt thereof, (ii) about 0.01 to 1.0% w/w hydroxypropyl methyl cellulose, (iii) about 0.068 to about 6.8% w/w of sodium chloride, (iv) about 0.0019 to about 0.19% w/w monobasic sodium phosphate, (v) about 0.005 to about 0.5% w/w disodium edetate, and (vi) about 0.0025 to about 0.25% w/w benzalkonium chloride, wherein the composition has a pH of 6.3 to 7.3.

16. The method of claim 15, wherein the hydroxypropylmethyl cellulose has a viscosity of 1 to 20 cPs.

17. The method of claim 15, wherein the viscosity of the composition is from about 1.5 to about 4.0 cPs.

18. The method of claim 15, wherein the composition, when intranasally administered, has an onset of action in less than 15 minutes.

19. A method of treating seasonal allergic rhinitis in a human patient in need thereof comprising nasally administering once daily about 342.5 mcg alcaftadine or a pharmaceutically acceptable salt thereof per nostril, wherein the alcaftadine is administered in a form of an aqueous pharmaceutical composition.

20. The method of claim 19, wherein the composition comprising a mucoadhesive agent.

21. The method of claim 20, wherein the viscosity of the composition is from about 1.5 to about 4.0 cPs.

22. A method of treating seasonal allergic rhinitis in a human patient in need thereof comprising nasally administering twice daily about 685 mcg alcaftadine or a pharmaceutically acceptable salt thereof per nostril, wherein the alcaftadine is administered in a form of an aqueous pharmaceutical composition.

23. The method of claim 22, wherein the composition comprising a mucoadhesive agent.

24. The method of claim 23, wherein the viscosity of the composition is from about 1.5 to about 4.0 cPs.

* * * * *